United States Patent [19]

Oester et al.

[11] Patent Number: 5,677,160

[45] Date of Patent: Oct. 14, 1997

[54] FAT SPLITTING PROCESS

[75] Inventors: Dean A. Oester, Cincinnati; Allen L. Hall, Amelia; Karl T. Zilch, Cincinnati; Kevin W. Anderson, Hamilton, all of Ohio

[73] Assignee: Henkel Corporation, Plymouth Meeting, Pa.

[21] Appl. No.: 356,047

[22] Filed: Dec. 14, 1994

Related U.S. Application Data

[63] Continuation of Ser. No. 40,250, Mar. 30, 1993, abandoned, which is a continuation-in-part of Ser. No. 428,522, Oct. 30, 1989, abandoned.

[51] Int. Cl.$^6$ ................................. C12P 7/62; C12P 7/48; C12N 9/20; C12N 1/00
[52] U.S. Cl. ........................ 435/198; 435/135; 435/144; 435/874; 435/931
[58] Field of Search ................................. 435/135, 144, 435/198, 874, 931

[56] References Cited

U.S. PATENT DOCUMENTS

| 2,486,630 | 3/1949 | Brown | 260/415 |
| 4,275,011 | 6/1981 | Tanaka | 260/410.7 |
| 4,275,081 | 6/1981 | Coleman et al. | 426/33 |
| 4,678,580 | 7/1987 | Brady et al. | 210/490 |
| 5,106,736 | 4/1992 | Patel et al. | 435/106 |

FOREIGN PATENT DOCUMENTS

| 0093602 | 11/1983 | European Pat. Off. |
| 0188725 | 7/1986 | European Pat. Off. |
| 0191217 | 8/1986 | European Pat. Off. |
| 2705608 | 2/1976 | Germany . |
| 3108927 | 9/1982 | Germany . |
| 62-228289 | 3/1986 | Japan . |
| 61-181390 | 8/1996 | Japan . |
| WO82/03873 | 11/1982 | WIPO . |
| WO83/0016 | 1/1983 | WIPO . |

OTHER PUBLICATIONS

Okumura, et al, "The Effect of Reverse Action on Triglyceride Hydrolysis by Lipase", *Agric. Biol. Chem.*, 45(1), 1981, pp. 185–189.

Lobyreva, et al, Institute of Microbiology, Academy of Sciences of the USSR, *Mikrobiologiya*, vol. 48, No. 1, 1979, pp. 53–56.

"Enzymatic Hydrolysis of Fats", *Henkel–Referate 23/Int. Ed.*, 1987, pp. 29–35.

Okumura, et l, "Purification and Properties of Partial Glyceride Hydrolase of Penicillium cyclopium M1", *J. Biochem.*, 87, 1980, pp. 205–211.

"Synthesis of Various Kinds of Esters by Four Microbial Lipases", *Biochimica et Biophysica Acta*, 575, 1979, pp. 156–165.

"Hydrolysis of Triglyceride by Solid Phase Lipolytic Enzymes of Rhizopus arrhizus in Continuous Reactor Systems", *Biotechnology and Bioengineering*, vol. XXIII, 1981, pp. 1703–1719.

"Combined Enzymatic/Non–Enzymatic Fat Spliting", *Research Disclosure*, vol. 310, #336102, Apr., 1992.

*Primary Examiner*—Michael G. Wityshyn
*Assistant Examiner*—Deborah K. Ware
*Attorney, Agent, or Firm*—Wayne C. Jaeschke; John E. Drach; Henry E. Millson, Jr.

[57] ABSTRACT

An improved fat splitting process which eliminates the induction period encountered during pressure splitting. A partial hydrolysis is conducted prior to pressure splitting by combining a lipase in the presence of water with the fat or oil to be hydrolyzed with added agitation. Pressure splitting of this partially split triglyceride eliminates or reduces the induction period.

19 Claims, 7 Drawing Sheets

FAT SPLITTING PROCESS

CROSS REFERENCE TO RELATED APPLICATIONS

This application is a continuation of application Ser. No. 08/040,250, filed Mar. 30, 1993, now abandoned, which is a continuation-in-part of application Ser. No. 07/428,522, filed Oct. 30, 1989, now abandoned.

FIELD OF THE INVENTION

This invention relates to improvements in the pressure splitting of fats and oils by means of a presplitting step utilizing lipase hydrolysis.

BACKGROUND OF THE INVENTION

Fatty acids are carboxylic acids having varying degrees of unsaturation and molecular weight. Fatty acids are used in a wide variety of products, such as in soaps and surfactants, lubricants, paints and coatings, candles, and in a variety of other agricultural, industrial, and personal care products. Glycerine, or 1,2,3-propanetriol, is used as humectant, plasticizer, emollient, and lubricant in a wide variety of industrial and personal care applications.

Though fatty acids and glycerine have been produced synthetically, a substantial portion of these materials are obtained from naturally derived fats and oils. Fats and oils are also know as triglycerides, which are the reaction products of an alcohol, glycerine, and an acid, the fatty acids discussed above. To produce fatty acids and glycerine from fats and oils, the fat or oil is hydrolyzed or "split", typically by the action of heat and pressure in the presence of water, to break the bonds between the acid and the alcohol.

Typically, the fat or oil is split commercially in a pressure splitter wherein preferably the fat or oil is introduced at one end and water introduced at the opposite end thereof in a countercurrent flow pattern. In operation, the pressure splitter provides substantial amounts of heat and pressure to the mixture of triglyceride and water to effect the hydrolysis. However, because the triglyceride is hydrophobic, the amount of actual contact between the water phase and the fat phase is relatively low. It is believed that after a period of time in the splitter individual triglyceride molecules incompletely hydrolyze, splitting off one acid molecule to create a di-glyceride or two acid molecules to form a monoglyceride. The mono- and di-glycerides are less hydrophobic than the starting triglyceride, and mix more thoroughly with water. As a result, the mono- and di-glycerides function as emulsifiers to improve mixing of the triglyceride with water. Under the turbulent conditions within the pressure splitter, it is believed that the mono- and di-glycerides improve the extent of mixing between the triglyceride and water, thereby facilitating the hydrolysis reaction.

The period of time during which the hydrolysis rate is depressed is known as the induction period. During the induction period, heat is input to the pressure splitter and pressure is generated, but few hydrolysis products are being produced. The volume of triglycerides hydrolyzed within the pressure splitter would be increased substantially if the induction period could be eliminated or at least substantially reduced.

Several methods have been used in the past to decrease the induction time in the pressure splitter. Surfactants have been added to the triglyceride feed to aid mixing between the water and fat layers in what became known as the Twitchell process. These surfactants were typically organo-sulphonic acids. However, after the splitting operation the surfactants had to be removed from the system, typically by extraction, which was time consuming and difficult to accomplish. Also, catalysts have been used to increase the rate of hydrolysis of the triglyceride and thereby the amount of mono- and di-glycerides. However, after the splitting operation was completed, the catalysts had to be removed from the system to eliminate undesirable contamination effects. It was also known that starting the pressure splitting operation with a fat or oil having a relatively high acid value would result in a decreased induction period in the splitting process. This could be accomplished by back-adding a blend of free acids, mono- and di-glycerides to the fat or oil feedstock. However, this step would not increase the overall efficiency of the pressure splitting process because a portion of the raw feedstock had to be replaced with the partially hydrolyzed portion. In effect, a portion of the feedstock had to be recycled through the splitter instead of subjecting the feedstock to splitting only once. In yet another method for decreasing the induction period, the feedstock in a storage tank prior to pressure splitting could be subjected to high temperatures in the presence of water to force the hydrolysis reaction to begin. However, the subjecting of the feedstock to such high temperatures, in the range above about 80° C., would cause formation of undesirable oxidation products and color bodies which would degrade the quality of the feedstock.

SUMMARY OF THE INVENTION

The invention relates to an improvement in the process of pressure splitting fats and oils which eliminates the induction period without the attendant disadvantages of previous methods. Specifically, the process employs a partial splitting step wherein a lipase with a minor amount of water is combined with the fat or oil feedstock with agitation prior to pressure splitting. The type of water used does not materially affect the reaction. Thus, distilled, tap or deionized water can be used with like effect. The partial splitting step is performed during that time while the fat or oil is stored in a holding tank prior to pressure splitting. The fat or oil is typically held in a heated tank for at least two days prior to pressure splitting, and partial hydrolysis can be performed within that period of time. Thus, the only additional costs associated with the partial hydrolysis are lipase costs, agitation cost and those costs connected with charging the lipase solution and later removing same after the partial hydrolysis, if that is desired. The lipase solution is agitated at a rate sufficient to render the solution miscible or finely dispersed in the feedstock. The agitation is continued for a period of time sufficient to raise the acid value, and at a temperature optimally just below the deactivation temperature of the lipase. It has been found that agitation of a tallow feedstock with lipase and water for about 24 to 48 hours at temperatures of up to about 60° C. can produce acid values in the range of about 40 to about 80 (mg KOH/g sample). In comparison, complete hydrolysis of tallow would produce an acid value from the liberated carboxylic acids of about 200.

The lipase is combined with the fat or oil feedstock in a preferred range of about 1 ppm to about 100 ppm total protein by weight of the feedstock. Levels of lipase outside this range may be used, as well as different lipase enzymes, so long as the amount and type is effective in producing a partial split acid value, preferably at least about 40. The upper acid value limit is dictated by the nature of the lipase reaction, which is discussed in more detail hereinbelow. The lipase is mixed with water prior to blending the feedstock.

It has been found that water becomes a limiting reactant at concentrations of 1% or less, based on volume per feedstock weight. Good results were obtained when the resultant aqueous phase comprises at least about 2.5% volume in milliliters per gram weight of the fat or oil feedstock.

The preferred lipase is a 1,3-position specific enzyme. This type of lipase cleaves the ester linkage at the 1 and 3 positions on the triglyceride, but leaves the remaining ester linkage intact. As a result, the hydrolyzed triglyceride molecule, now a monoglyceride, carries the glycerine portion along in the fat layer instead of the water layer. The advantage of carrying the glycerine substituent with a single carboxylic acid molecule is discussed in more detail hereinbelow. In addition to the 1,3-specific enzyme, two other types of lipase are available—a position non-specific enzyme and a chain length-specific enzyme. The non-specific enzyme cleaves all three ester linkages in the triglyceride. The chain length-specific enzyme cleaves only those triglycerides having a chain length within a certain range. These types of enzymes also are useful under the teachings of the invention. The selection of lipase specificity will be dependent on the chain length distribution of the fat or oil substrate, the mechanics of changing from the lipase pre-splitting operation to the high pressure splitting operation and whether the high pressure splitting is being done in a batch or continuous mode.

It is an object of this invention to provide a fat or oil splitting process utilizing a pressure splitting operation which eliminates or minimizes the induction period.

It is an additional object of the invention to hydrolyse a fat or oil feedstock prior to pressure splitting using materials which do not require subsequent removal from the treated feedstock.

It is yet a further object of the invention to provide a partial splitting step which modifies the triglyceride and thereby allows for efficient utilization of the pressure splitting operation.

It is yet a further object of the invention to partially hydrolyze triglycerides in a manner to minimize formation of free glycerine prior to pressure splitting.

The above objects, as well as other objects and advantages of the invention, are more thoroughly described in the detailed description of the invention and the drawings, of which:

DETAILED DESCRIPTION OF THE INVENTION

The invention in its broader aspects relates to a method of increasing the production of carboxylic acids and glycerine from glycerides in a pressure splitter comprising the combining in a first step of the glycerides with a suitable amount of an effective lipase with agitation in the presence of water to partially split the glycerides, and mixing the partially split glycerides in the pressure splitter with water under conditions of temperature and pressure effective to substantially complete the splitting of the glycerides into component carboxylic acids and glycerine, wherein the production of the carboxylic acids and glycerine from the partially split glyceride is increased relative to a glyceride not treated with the lipase. Preferably, the lipase is derived from *Humicola lanuginosa*. This lipase is a 1,3-position specific enzyme. The enzyme, as discussed above, cleaves the triglyceride preferentially at the 1 and 3 positions on the glycerine molecule, leaving a monoglyceride after hydrolysis. The monoglyceride tends to stay in the fat layer as opposed to the aqueous layer bearing the enzyme. Since the pressure splitting results in formation of lipophilic fatty or carboxylic acids and hydrophilic glycerine, it is preferred from a process standpoint that the glycerine from the presplitting step also be sent to the pressure splitter, so that there needs to be only one glycerine-water, or "sweat-water", take-off. Practically, some glycerine is released during the presplit step because of rearrangement of the carboxylic acid-glycerine bond from the "2" position to either the "1" or "3" positions on the glycerine molecule, but this amount is substantially reduced relative to the amount generated were a non-specific lipase to be used. This lipase is not completely resistant to inactivation by impurities in the triglyceride starting materials, which may be present for example as bacterial decomposition products from proteins present in rendered tallow, a commonly used triglyceride starting material.

Another preferred lipase is the lipase derived from Pseudomonas sp. ATCC #21808. This lipase is more thermally stable than other lipases in the practice of the invention, i.e. this lipase can be employed at temperatures of up 76° C., which is a temperature at least 16° C. higher than the temperatures at which other lipases can be employed. At a temperature of 75° or 76° C. this lipase can cleave the triglyceride to an acid value of 90 in less than 48 hours. In addition, the lipases derived from Pseudomonas species, especially sp. ATCC #21808 are resistant to inactivation by impurities in the triglyceride starting materials. Lipases derived from Pseudomonas species are commercially available from Amano International Enzyme Company, Inc. as Amano Lipase AK or Amano Lipase PS 30.

Another lipase that can be employed herein is lipase derived from *Mucor miehei* commercially available from the Amano International Enzyme Company, Inc. as Amano Lipase M and from Novo Industries as Novo PALATASE™ lipase.

The triglyceride partially split by lipase may be transferred to the pressure splitter with or without the residual lipase solution. The lipase solution can be removed by phase separation, for example by centrifugation or by settling under gravity, prior to pressure splitting for recycling to effect the hydrolysis of other triglycerides. Alternatively, because the lipase deactivates under the strenuous conditions in a pressure splitter, the solution may be transferred into the splitter with the glyceride with no ill effect.

In addition to the batch process for the above lipase presplitting of triglycerides, it has been found that significant advantages result from carrying out lipase presplitting in a continuous process.

One major and unexpected advantage of such a continuous process is the discovery that even where impurities are present in the triglyceride starting material which would tend to inactivate at least some lipases in a batch process, such inactivation does not occur in a continuous process, for reasons that are not clearly understood, but may be connected with the backmixing conditions that occur in a continuous process.

A continuous lipase presplitting process for triglycerides can be carried out as follows. A triglyceride to be treated, such as tallow, is introduced continuously into a reaction vessel at an elevated temperature, e.g. at about 50°–60° C. A lipase slurry in water containing from about 0.01% to about 2%, preferably about 0.08% to about 1.2% by weight of lipase is simultaneously introduced on a continuous basis into the reaction vessel. The flow rates of the triglyceride and of the tallow slurry are adjusted to provide from about 2% to about 5% by weight of water based on the weight of triglyceride, and to provide a residence time for the triglyceride in the reaction vessel of from about 24 to about 96 hours, depending on the temperature and on the activity of the lipase used in the process. Under these conditions, a steady state acid value in the effluent ranging from about 25 to about 100 is obtained, and usually from about 50 to about 100. The mixture in the reaction vessel is thoroughly mixed throughout the process, using any agitation or stirring means that will accomplish such thorough mixing. The effluent presplit triglyceride can then be processed directly in a pressure splitter.

Optionally, the residual water of hydrolysis, containing both free glycerine and lipase activity, may be recovered by phase separation. This separation can be done external to the presplitting reactor, for example using a centrifuge or under gravity using an auxiliary settling tank. The resulting dewatered light phase is processed in a pressure splitter. The heavy sweatwater phase can be partially recycled to the presplitting reactor to reuse some of the residual lipase activity.

Alternatively, to achieve recycle of residual lipase, the phase separation can be carried out internal to the presplitting reactor by forming a quiescent settling zone inside the presplitting reactor, below the location where presplit effluent is withdrawn from the reactor. Any arrangement having a hydraulic radius sufficiently large such that the terminal settling velocity of the water droplets that coalesce in the quiescent zone exceeds the upward velocity of the presplit fat can be used. An auxiliary effluent exit location is provided for removing the presplit triglycerides from the reactor contents. Any desired recycle ratio can be achieved by balancing the rate that presplit triglycerides are removed from above the settling zone with the rate effluent is withdrawn from the reactor.

The operation of commercial pressure splitters is well known in the industry. Essentially, triglyceride in the form of an oil, molten fat, or a blend thereof is introduced into a reactor with water, and heat is applied. As the temperature increases, so does the pressure. In batch splitters, the components are mixed by agitation. In continuous splitters, the triglyceride is typically introduced from the bottom, water from the top, and the difference in densities and the input pumping force causes mixing. Temperatures in the continuous pressure splitters range from about 200° to about 300° C., preferably about 250° to about 280° C., and the pressure within the reactor ranges preferably from about 550 to about 950 psi. The triglyceride is mixed in the continuous splitter with water, which comprises about 40 to about 50% by weight of the reactor contents. On a laboratory scale, the pressure splitting was conducted as a batch process. Batch pressure splitting involves temperatures in the range of about 240° to about 260° C., and pressures preferably in the range of about 450 to about 700 psi. Water content in the batch process is slightly higher, in the range of about 50 to about 70% by weight of the reactor contents.

Figure 1:
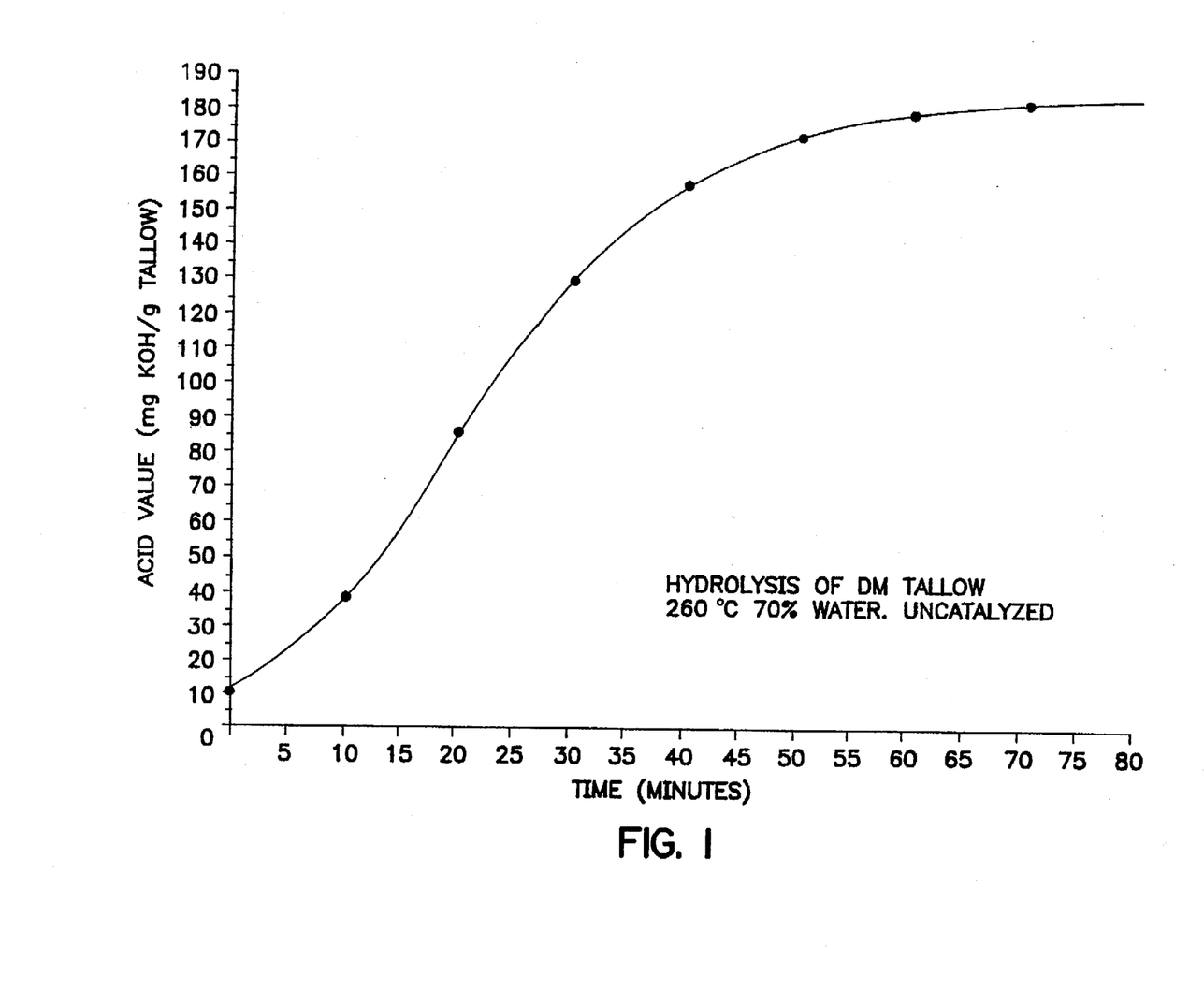
FIG. 1 is a graph depicting the change in acid values with time for hydrolysis of tallow in a conventional batch pressure splitter.

The reaction rate of hydrolysis of triglycerides in a pressure splitter does not proceed linearly with time. Rather, a plot of acid value versus time is sigmoidal in shape. A representative curve of the pressure splitting of tallow is shown as FIG. 1. In the lower left-hand portion of the curve, the rate of change of acid value calculated as milligrams of potassium hydroxide needed to neutralize a known weight of sample in grams is depressed relative to the middle of the curve. This initial period wherein the acid value changed but slightly with time is known as the induction period. In FIG. 1, it can be seen that the slope of the curve changes markedly beginning at an acid value of approximately 40, which is the beginning of that period during which the reaction proceeds most quickly.

To obtain maximum efficiency from the pressure splitter, then, it is desired that the acid value of a triglyceride feedstock entering the splitter be at least about 40, and preferably from about 50 to about 100. To achieve this acid value with corresponding production of mono- and diglycerides, the lipase treatment is employed.

Figure 2:
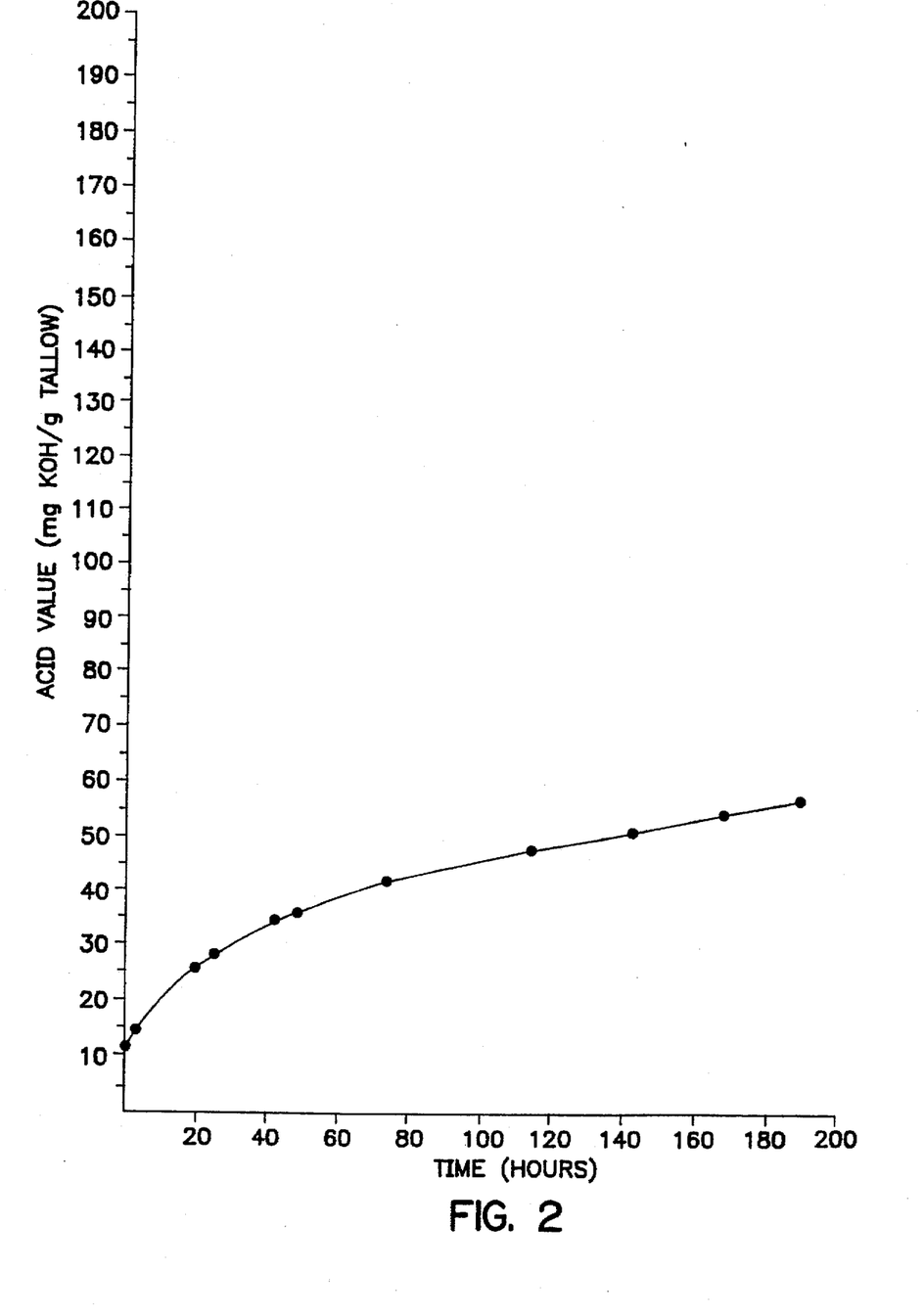
FIG. 2 is a graph depicting the change of acid value with time during the partial hydrolysis of tallow using a lipase derived from *Humicola lanuginosa*.

It is known that lipases hydrolyze glycerides to form carboxylic acids and free glycerine. However, lipases do not efficiently hydrolyze glycerides completely. Rather, an equilibrium is created wherein after a certain amount of hydrolysis of the glycerides takes place, the reverse reaction of esterification of the free carboxylic acids and glycerine occurs. The end result is that an equilibrium mixture of triglyceride, diglyceride, monoglyceride, carboxylic acids and glycerine is produced, requiring further modification to the system to drive the reaction to complete hydrolysis. This effect can be seen by referring to FIG. 2, wherein about 0.05 g granular $Humicola$ $lanuginosa$-derived LIPOLASE™, 30T lipase, a product of Novo Industries, more fully described below, was added to 500 g DM tallow and 25 g distilled water and agitated at 60° C. at a rate sufficient to maintain miscibility between the oil and aqueous phases, typically involving recirculation of the mixture volume about four times per hour. One method of driving the reaction is to remove the reaction products, i.e., the carboxylic acids and glycerine. However, such removal requires subjecting the reaction mixture to temperatures which deactivate the enzyme or to conditions which adversely affect the yield of the reaction products. Additional explanation is provided in the article "Enzymatic Hydrolysis of Fats", pp. 29–35, Henkel-Referate 23/Int. Ed. (1987), herein incorporated by reference. This article is an abridged version of the paper "Enzymatische Fettspaltung" published in $Fett$ $Wissenschaft$ $Technologie$, V. 89, p. 156 (1987). Thus, though both hydrolysis via treatment with lipase and hydrolysis via pressure splitting convert triglycerides to carboxylic acids and glycerine, both have inherent disadvantages which inhibit their most efficient use.

For a bath process, the partial splitting of triglyceride utilizing lipase is conducted at a temperature below the deactivation temperature of the lipase in a storage vessel with air atmosphere such as a holding tank in the presence of water and with agitation. Agitation is important to maximize the interfacial surface of the lipase, which is in the water phase, with the hydrophobic triglyceride. Satisfactory results were obtained by agitating the triglyceride and lipase solution at a rate sufficient to maintain miscibility of the phases. It was found that a rate providing recirculation of the reactor volume about four times in an hour was satisfactory.

It is believed that the process of partial splitting combined with pressure splitting will be applicable to effecting hydrolysis of any glyceride molecule having an ester linkage. The process is intended to be especially useful in hydrolyzing tallow, lard, coconut oil, canola oil, palm oil, and mixtures thereof.

Operating Examples

The following detailed operating examples illustrate the practice of the invention in its most preferred form, thereby enabling a person of ordinary skill in the art to practice the invention. The principles of this invention, its operating parameters and other obvious modifications thereof will be understood in view of the following detailed procedure.

Pressure splitting in the laboratory was conducted in one liter Autoclave Engineers (AE) stainless steel (SS) autoclaves equipped with magnetic agitators. Water and triglyceride were heated to the reaction temperature of 260° C. in separate autoclaves, the triglyceride-containing autoclave being mounted above the other. Reaction was initiated by forcing heated triglyceride via a bottom take-off into the autoclave containing the water by pressurizing the triglyceride autoclave with nitrogen. The resulting pressure after combination of the water and triglyceride was about 700 psi. Where desired, timed samples were removed through a valved dip tube in the water-containing autoclave.

EXAMPLE 1

The following reactions were run to demonstrate the effect of lipase on triglyceride. Distillation mix tallow (DM tallow), a blend of Bleachable Fancy, Prime and Low Acid Special tallows, was reacted with LIPOLASE™ 30T, a 1,3-position specific detergent lipase having a broad pH and temperature range from Novo Industries. LIPOLASE™ 30T lipase is derived from *Humicola lanuginosa* which is expressed in *Aspergillus oryzae*, which serves as the production strain for the lipase. The LIPOLASE™ 30T lipase has a granulated form which is comprised essentially of a blend of cellulosic material, lipase, and titanium dioxide. Reactions were carried out with 200 gram samples of tallow mechanically agitated at 45° C. in round bottom flasks in an air atmosphere. Table 1 below lists the lipase weight, water phase volume, and acid value of the tallow after 24 hours agitation at 300 rpm.

TABLE 1

| Reaction | Enzyme Weight (grams) | Aqueous Phase (% v/w tallow) (in ml H$_2$O/g tallow) | Acid Value (24 hours) (mg KOH/g sample) |
|---|---|---|---|
| 1 | — | 5.0 | 6.7 |
| 2 | 0.1007 | 5.0 | 67 |
| 3 | 0.0135 | 5.0 | 28 |
| 4 | 0.0305 | 5.0 | 42 |
| 5 | 0.0152 | 2.5 | 34 |
| 6 | 0.0338 | 2.5 | 41 |

EXAMPLE 2

To demonstrate the importance of agitation toward effecting partial hydrolysis of tallow, 100 gram samples of DM tallow were mixed with 0.01 grams of Lipolase 30T dissolved in 5 ml distilled water. Table 2 below demonstrates the effect different agitation rates had on the resulting acid value of the partially hydrolyzed tallow.

TABLE 2

| Agitation | Acid Value 24 hours | (mg KOH/g sample) 48 hours |
|---|---|---|
| none | 13.1 | 14.0 |
| 100 rpm | 38.8 | 46.1 |
| 200 rpm | 41.6 | 53.1 |
| 300 rpm | 41.2 | 58.2 |

EXAMPLE 3

Free glycerine analyses were conducted on both agitated and unagitated 200 g DM tallow samples mixed with 0.02 grams of Novo LIPOLASE™ 30T lipase dissolved in 10 ml of tap water. These tests were run to determine whether the LIPOLASE™ 30T lipase was operating as a 1,3-position specific lipase. If the enzyme cleaved the ester linkages at only the "1" and "3" positions, the amount of free glycerine would be very low. The glycerine would be able to be carried into the pressure splitter in the oil phase. The partial splitting reactions were run for various lengths of time at 60° C. In Table 3 below, reaction time and agitation rate were varied, and the free glycerine levels and acid values are listed for the various experimental conditions.

TABLE 3

| Reaction Time | Sample 1 No Agitation | | Sample 2 Agitation, 300 rpm | |
|---|---|---|---|---|
| | AV | wt. % glycerine* | AV | wt. % glycerine* |
| 0.1 hr | 11.2 | 0.003 | 12.0 | 0.008 |
| 3.0 | 11.4 | 0.007 | 13.6 | 0.008 |
| 19.0 | 13.1 | 0.005 | 25.6 | 0.020 |
| 24.0 | 13.1 | 0.006 | 30.3 | 0.041 |
| 46.0 | 14.0 | 0.006 | 40.5 | 0.061 |

*wt. % free glycerine based on sample mass

The free glycerine analyses were conducted using Method Ca 14-56 from The American Oil Chemists' Society. The maximum amount of glycerine in DM tallow was calculated to be approximately 10% by weight. In sample 2, an acid value of 40.5 for DM tallow corresponds to approximately 20% split of the fat. If the LIPOLASE™ 30T lipase was in fact a non-specific lipase, one would expect the release of approximately 20% of the available glycerine. Clearly, only very slight amounts of free glycerine were released by the hydrolysis. This verified that the LIPOLASE™ 30T lipase was in fact a 1,3-position specific lipase. The presence of the minor amounts of free glycerine indicates that interesterification of a 2-acyl glyceride to a 1- or 3-position is occurring, but not at a significant rate.

The experiments were conducted using LIPOLASE™ 30T lipase, derived from *Humicola lanuginosa*, which caused acceptable increases in acid value in relatively short periods of time at a reasonable processing cost. However, it is expected that other lipases, such as those derived from *Candida cylindracea* commercially available from Sigma Chemical Co. as L-1754 lipase or *Rhizopus arrhizus* commercially available from Sigma Chemical Co. as L-4384 lipase and from the Amano International Enzyme Company, Inc. as Amano Lipase N Lipase, Amano Lipase O lipase, and Amano Lipase F lipase, as well as other lipases discussed earlier, can be used to perform the necessary hydrolysis.

EXAMPLE 4

Increased batch high pressure splitting when using lipase presplit tallow.

Figure 3:
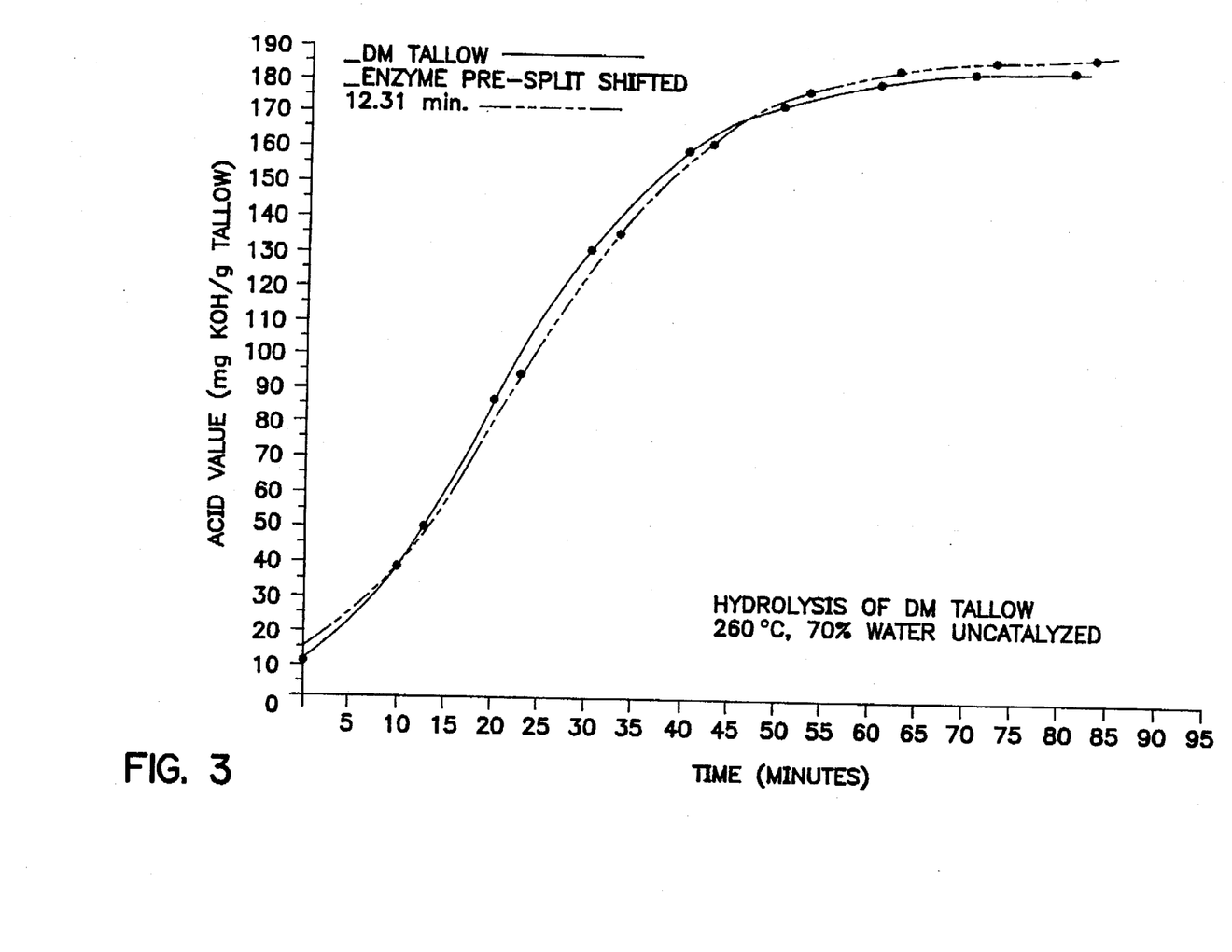
FIG. 3 is a graph depicting the effect of partial splitting using lipase on the hydrolysis of glycerides in a batch pressure splitter.

The use of a lipase-induced partial split increases the operating efficiency of the pressure splitter by allowing the pressure splitter to begin hydrolyzing glycerides at acid value levels which fall into the most effective portion of the pressure splitter rate curve. The partial split modifies the triglyceride feedstock to minimize residence time and also substantially eliminate the induction period. However, the lipase-induced partial split does not increase the rate of hydrolysis of triglyceride in the pressure splitter. As can be seen in FIG. 3, by shifting by 12.31 minutes the pressure splitting curve of DM tallow after a partial split which raised the acid value to about 45 using LIPOLASE™ 30T lipase, the curves for pressure splitting of the DM tallow both with and without partial splitting are essentially superimposable. The batch splitting process reaches an equilibrium state acid value after approximately 80 minutes, which corresponds to about 95% hydrolysis completion. The time savings noted above corresponds to an improvement of about 15% in the time needed to effect substantially complete hydrolysis of the triglyceride in the batch splitter. It is expected that similar time savings will be experienced in the operation of continuous pressure splitter equipment.

EXAMPLE 5

Batch process for lipase presplitting of animal fats and subsequent processing on a pressure splitter.

Approximately 1.8 million pounds of animal fat, comprised essentially of beef and pork fats, was charged to a tank reactor equipped with a side mounted agitator. Water was added to the fat to give a moisture content of 3.2% at a temperature of 136° F. The acid value of the fat mixture was 11.3.

Figure 4:
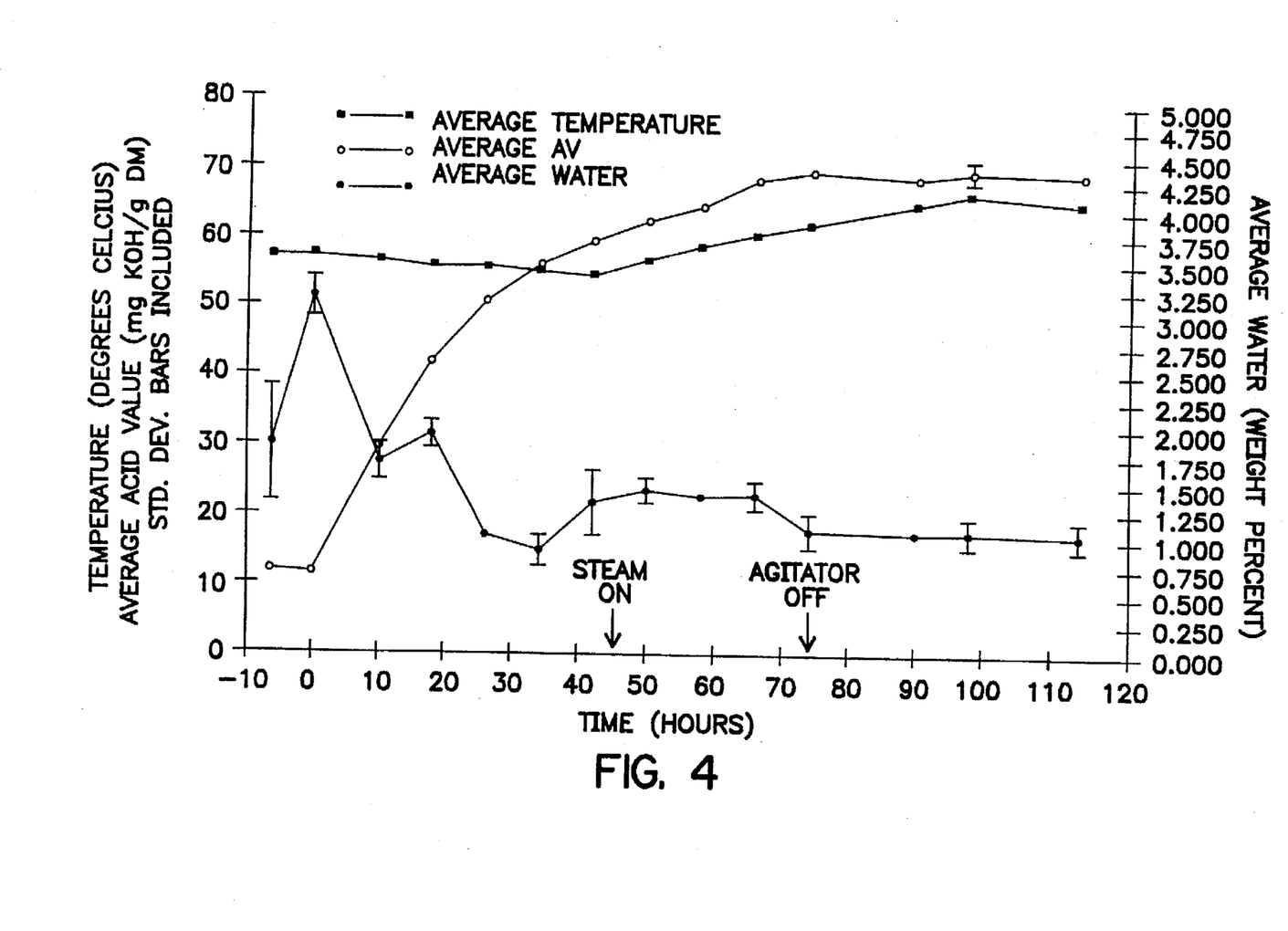
FIG. 4 is a graph depicting the partial hydrolysis of DM tallow using a lipase.

A slurry, consisting of 260 lb. LIPOLASE™ 30T lipase and approximately 75 gallons of tap water, was prepared in a small tank agitated by hand, and then pumped into the reactor. The resulting progress of the presplitting reaction is shown in FIG. 4. The acid value rose to about 70 after 70 hours, after which agitation was stopped and the residual water containing residual lipase activity and free glycerine was settled and processed separately.

The presplit and dewatered fat was processed in a high pressure splitter. It was observed that this fat was processed 15% faster than similar non-presplit fats.

EXAMPLE 6

Batch process for lipase presplitting of animal fats and subsequent processing in a pressure splitter.

Another batch of animal fat as in Example 5 was presplit according to the process of Example 5 to an acid value of 78–80. When processed in a different pressure splitter, the presplit fat processed 30% faster than similar non-presplit fats in this pressure splitter.

EXAMPLE 7

Batch process for lipase presplitting of coconut oil and subsequent processing on a pressure splitter.

Approximately 893,000 pounds of coconut oil was charged to a tank. 35,300 lbs. of water was added batchwise to the tank and agitated by recirculation through a nearby service pump. The temperature was maintained at about 100° F.

Figure 5:
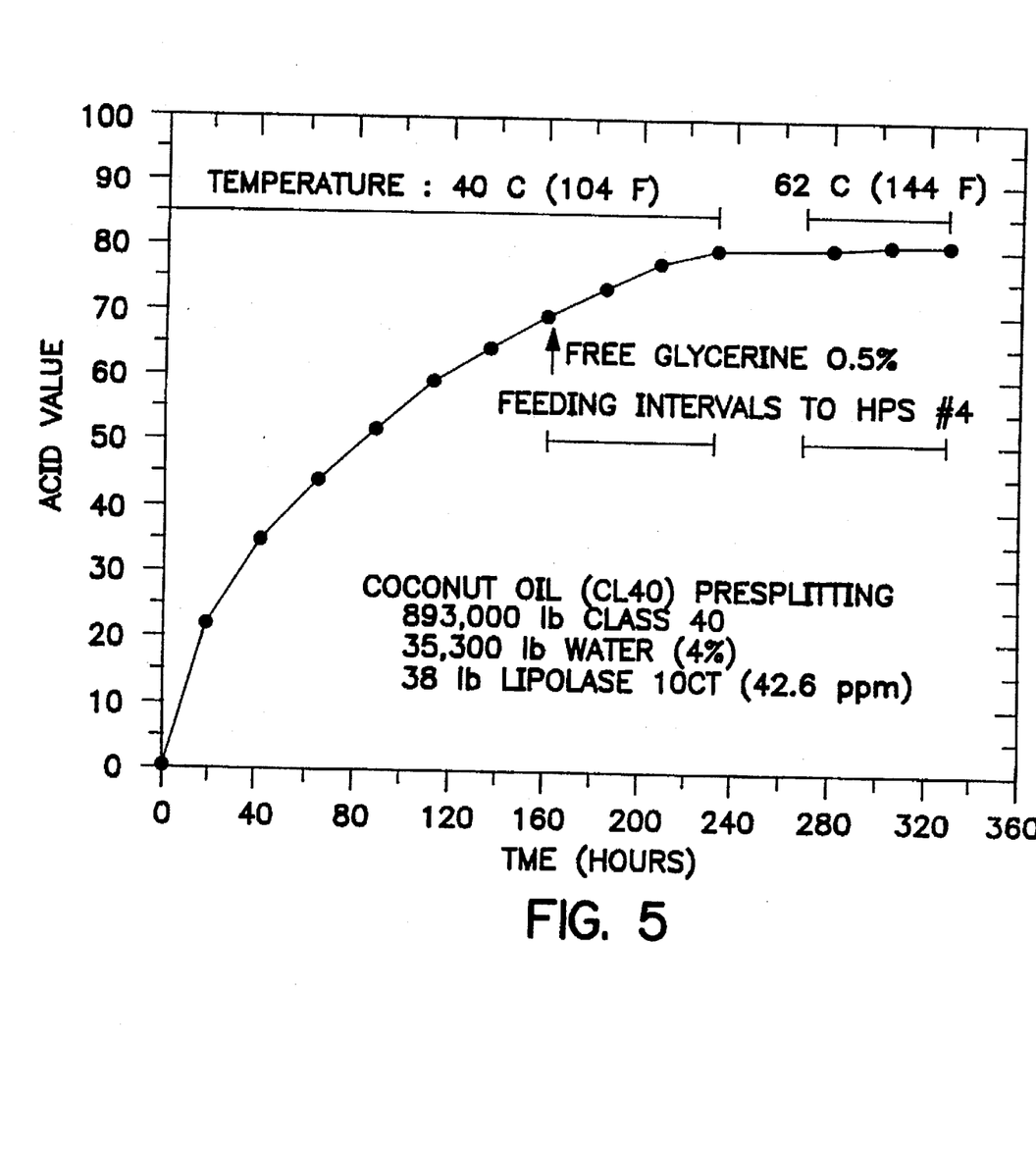
FIG. 5 is a graph depicting the partial hydrolysis of coconut oil using a lipase.

LIPOLASE™ 100T lipase, a product of Novo Industries was slurried in tap water (20 gallons) using a large spatula. The slurry was bailed into the oil/water mixture using buckets. The progress of this presplitting reaction is shown in FIG. 5 in which the acid value rose to between 70 and 80. The hydrolysis reaction was much slower than in Example 6 due to the significantly poorer mixing conditions in the presplitting vessel.

The resulting presplit coconut oil-water mixture was then processed in a pressure splitter at a rate 19%–26% faster than similar non-presplit coconut oil in this pressure splitter.

EXAMPLE 8

Pilot plant continuous lipase presplitting process.

Figure 6:
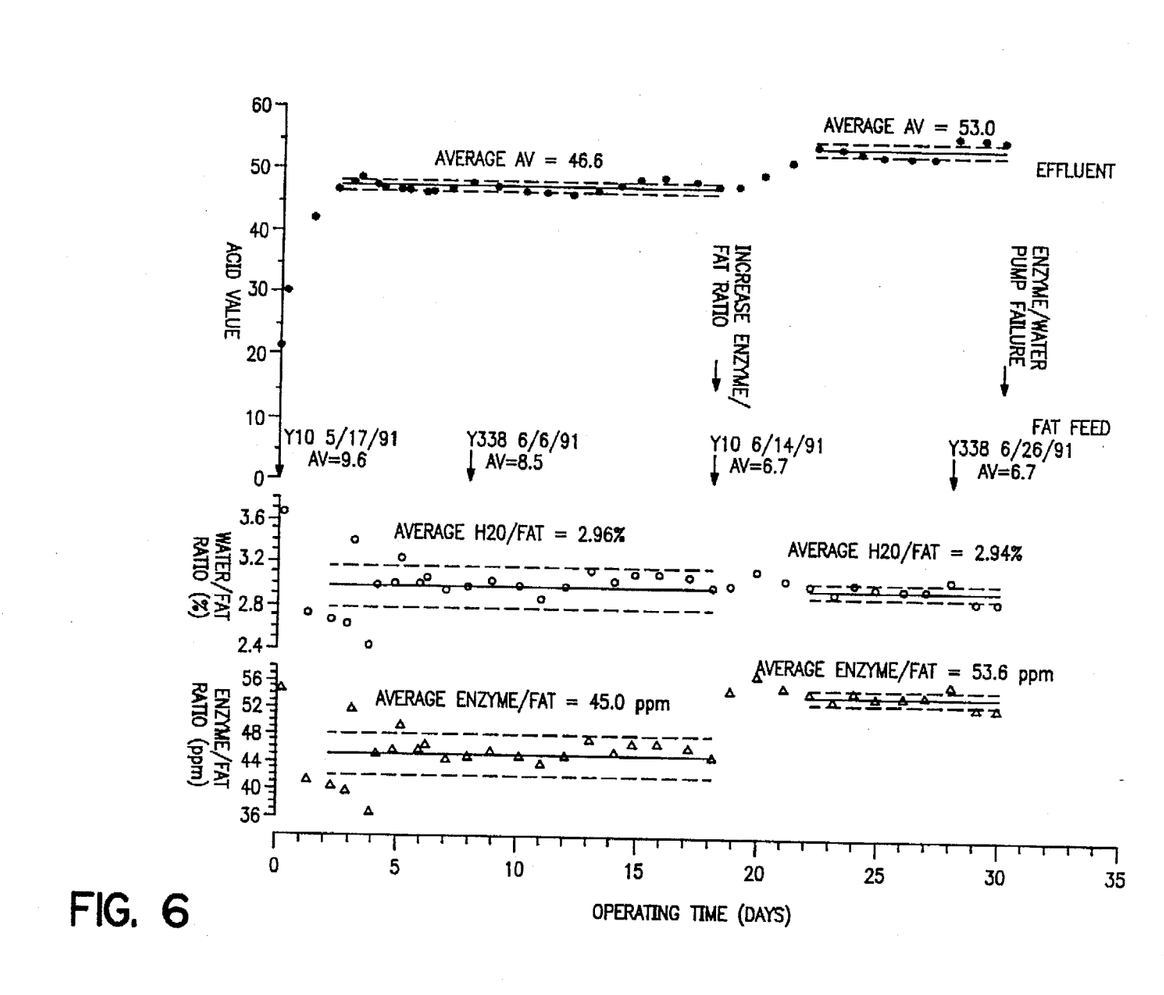
FIG. 6 is a graph depicting the continuous lipase presplitting of animal fats.

An agitated pilot plant reactor was charged with 22.9 lbs. of animal fat comprised essentially of pork and beef fats. Water (3% w/w) and Novo LIPOLASE™ 100T lipase (43 ppm w/w) were then added. Fat feed was also started (0.249 lb/hr) along with a water slurry of Lipolase™ 100T to give an average water/fat feed ratio of 2.95% and an average enzyme/fat feed ratio of 45.0–53.6 ppm. FIG. 6 shows the steady state operation of continuous presplitting over a period of 30 days (after a nominal start-up and one step-change transient).

Figure 7:
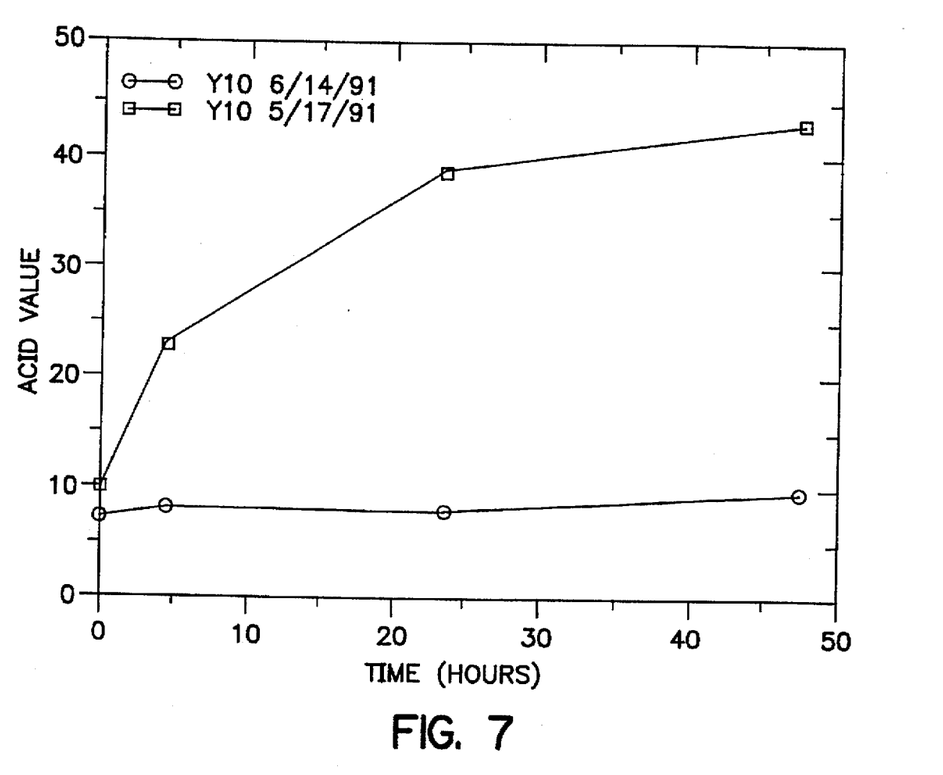
FIG. 7 is a graph depicting the kinetics of animal fats used in a continuous lipase presplitting process.

It was observed that fats possessing inhibitory properties toward the lipase do not influence the operation of the continuous process. For example, the batch presplitting kinetics obtained in an independent 48 hr experiment for the sample labeled Y10 5/17/91 is compared with the kinetics obtained with the sample labeled Y10 6/14/91 (FIG. 7). As shown in FIG. 7, the tallow from Y10 6/14/91 does not presplit with LIPOLASE™ 100T lipase in a batch process. However, no detrimental effect was observed in the performance of the continuous presplitting process (FIG. 6).

Thus it is apparent that there has been provided, in accordance with the invention, an improved fat splitting process that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications and variations as they fall within the spirit and broad scope of the appended claims.

What is claimed is:

1. A process for the production of carboxylic acids and glycerine from a glyceride comprising the steps of
   a) mixing the glyceride with agitation at atmospheric pressure and in the presence of water with an effective lipase in an amount sufficient to produce partial splitting of the glyceride, and
   b) mixing the partially split glyceride in a pressure splitter with water at a temperature in the range of from about 200° to about 300° C. and at a pressure in the range of from about 450 to about 950 psi to hydrolyze the glyceride into carboxylic acids and glycerine.

2. The process of claim 1 wherein said temperature in said pressure splitter is in the range of about 240° to about 280° C.

3. The process of claim 1 wherein said water in step (a) comprises at least 2.5 wt. % based on said glyceride.

4. The process of claim 1 wherein said glyceride is selected from the group consisting of tallow, lard, coconut oil, canola oil, palm oil, and mixtures thereof.

5. The process of claim 1 wherein step (a) is conducted at a temperature less than 70° C.

6. The process of claim 1 wherein said agitation recirculates the volume of said glyceride, said lipase and said water in step (a) at least four times per hour.

7. The process of claim 1 wherein said lipase is a 1,3-position specific enzyme.

8. The process of claim 1 wherein said partially split glyceride has an acid value of from about 25 to about 100.

9. The process of claim 8 wherein said acid value is from about 40 to about 100.

10. The process of claim 1 wherein step (a) is carried out as a continuous process.

11. The process of claim 1 wherein step (a) is carried out as a batch process.

12. The process of claim 1 wherein the glyceride is a naturally derived oil or fat, or a mixture thereof.

13. The process of claim 1 wherein in step (a) the lipase is derived from the genera Mucor, Candida, Rhizopus, Humicola, Aspergillus, or Pseudomonas.

14. The process of claim 13 wherein the lipase is derived from *Mucor miehei, Candida cylindracea, Rhizopus arrhizus, Humicola lanuginosa*, or *Pseudomonas sp*, ATCC 21808.

15. The process of claim 1 wherein in step (a) the lipase is derived from *Humicola lanuginosa*.

16. The process of claim 1 wherein step (b) is carried out at least 15% faster than pressure splitting without using step (a).

17. A process for the production of carboxylic acids and glycerine from a glyceride comprising the steps of a) mixing the glyceride with agitation at atmospheric pressure and in the presence of water with from about 1 ppm to about 100 ppm based on the weight of glyceride of a lipase at a temperature below the deactivation temperature of said lipase to partially split the glyceride to obtain an acid value therefore of from about 25 to about 100; and b) mixing the partially split glyceride in a pressure splitter with water, wherein the partially split glyceride and the water are subjected to a temperature in the range of from about 200° to about 300° C. and a pressure in the range of from about 450 to about 950 psi to hydrolyze the glyceride into carboxylic acids and glycerine.

18. The process of claim 17 wherein step (a) is carried out as a continuous process.

19. The process of claim 17 wherein in step (a) the lipase is derived from *Mucor miehei, Candida cylindracea, Rhizopus arrhizus, Humicola lanuginosa*, or *Pseudomonas sp*, ATCC 21808.

* * * * *